United States Patent [19]

Volante et al.

[11] Patent Number: 4,611,067

[45] Date of Patent: Sep. 9, 1986

[54] PROCESS FOR THE PREPARATION OF HMG-COA REDUCTASE INHIBITORS AND INTERMEDIATE COMPOUNDS EMPLOYED THEREIN

[75] Inventors: Ralph P. Volante, East Windsor; Thomas R. Verhoeven, Cranford; Meyer Sletzinger, North Plainfield; James M. McNamara, Rahway; Thomas M. H. Liu, Westfield; Edward G. Corley, Old Bridge, all of N.J.

[73] Assignee: Merck & Co., Inc., Rayway, N.J.

[21] Appl. No.: 696,963

[22] Filed: Jan. 31, 1985

[51] Int. Cl.[4] .................. C07D 309/30; C07C 102/08; C07C 102/00; C07C 103/167; C07C 103/173

[52] U.S. Cl. .................... 549/292; 564/129; 564/158; 558/405; 556/416; 549/419

[58] Field of Search .............. 549/292, 419; 564/129, 564/158; 260/465 F; 556/416

Primary Examiner—Norma S. Milestone
Attorney, Agent, or Firm—Joseph F. DiPrima; William H. Nicholson; Michael C. Sudol

[57] ABSTRACT

This invention relates to a novel process for the preparation of 3-hydroxy-3-methylglutarylcoenzyme A (HMG-CoA) reductase inhibitors which contain a 4-hydroxy-3,4,5,6-tetrahydro-2H-pyran-2-one moiety, such as compactin and mevinolin, by utilizing an alkyl 4-cyano-3(R)-hydroxybutanoate as a chiral synthon for the stereospecific introduction of the 4-hydroxy-3,4,5,6-tetrahydro-2H-pyran-2-one moiety.

9 Claims, No Drawings

PROCESS FOR THE PREPARATION OF HMG-COA REDUCTASE INHIBITORS AND INTERMEDIATE COMPOUNDS EMPLOYED THEREIN

BACKGROUND OF THE INVENTION

Endo et al., *J. Antibiotics*, XXIX, 1346 (1976) described a fermentation product, ML-236B, with potent antihypercholesterolemic activity which acts by inhibiting HMG-CoA reductase. This material, named compactin by Brown et al., *J. Chem. Soc., Perkin I*, 1165 (1976) was shown to have a desmethyl mevalonolactone partial structure and the stereochemistry was studied.

Shortly thereafter a chemically similar, natural product MK-803 (mevinolin), obtained by fermentation, was isolated and characterized, by Monaghan et al., U.S. Pat. No. 4,231,938. It has been shown to have the same desmethyl mevalonolactone partial structure and the absolute stereochemical configuration has been determined and described in EPO publication No. 0,022,478 of Merck & Co., Inc.

Totally synthetic analogs of these natural inhibitors have been prepared and described in Sankyo's U.S. Pat. No. 4,198,425 and Sankyo's U.S. Pat. No. 4,255,444 with no attempt being made to separate to stereo- and optical isomers. Subsequently, as described in Merck's EPO publication No. 0,024,348 and by Meyer, *Ann. Chem.*, (1979), pages 484–491, similar totally synthetic analogs were separated into their stereoisomers and optical enantiomers. Furthermore, it was shown in EPO publication No. 0,024,348 that essentially all of the HMG-CoA reductase activity resides in the 4(R)-trans species as in the case with the naturally occurring compounds compactin and mevinolin.

In most of the prior art processes for preparing the totally synthetic compounds, the lactone moiety of each compound had to be elaborated by a lengthy series of synthetic operations followed by very tedious and expensive chromatographic separation of the cis, trans racemates, or enantiomers, following which, the inactive cis-isomer would be discarded.

A process for the preparation of the lactone ring system in the correct optically active form was recently reported by Majewski et al., *Tetrahedron Lett.*, 1984, 2101–2104 utilizing a (3S,5S) iodoketal of the following formula:

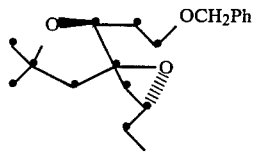

I

Additionally, a process for the preparation of HMG-CoA reductase inhibitors using alkyl 5(R),6-epoxy-3(R)-(alkoxy)hexanoate as a chiral synthon for the stereospecific introduction of 4-hydroxy-3,4,5,6-tetrahydro-2H-pyran-2-one moiety is disclosed and claimed in U.S. patent application Ser. No. 673,231, filed Nov. 19, 1984.

Further, filed contemporaneously herewith is U.S. patent application Ser. No. 696,965 wherein a process for the preparation of HMG-CoA reductase inhibitors using alkyl 4-halo-3(S)-hydroxybutanoate as a chiral synthon for the 4-hydroxy-3,4,5,6-tetrahydro-2H-pyran-2-one moiety is described and claimed.

DETAILED DESCRIPTION OF THE INVENTION

This invention relates to a novel process for the preparation of antihypercholesterolemic agents of the following general structural formula (I):

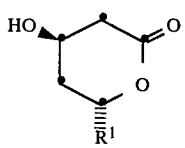

wherein $R^1$ is selected from the group consisting of:
(a)

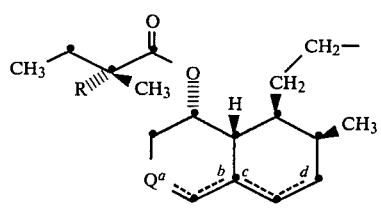

wherein
Q is

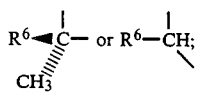

$R^6$ is H or OH;

R is hydrogen or methyl, and a, b, c, and d represent optional double bonds, except when a and c are double bonds, $R^6$ is not OH, especially wherein b and d represent double bonds or a, b, c, and d are all single bonds; or (b)

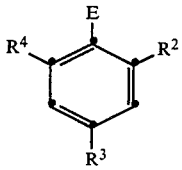

wherein E is —CH$_2$—, —CH$_2$CH$_2$— or —CH=CH—; $R^2$ and $R^3$ are independently C$_{1-3}$ alkyl or halo (F, Cl or Br) and $R^4$ is hydrogen, phenyl, benzyloxy, substituted phenyl or substituted benzyloxy in which the phenyl group in each case is substituted with one or more substituents selected from C$_{1-3}$ alkyl and halo, which comprises:

(A) reacting a compound of the formula (II):

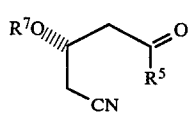

(II)

wherein $R^5$ is $C_{1-5}$ alkyloxy, benzyloxy or 2-thiopyridinyl and $R^7$ is $C_{1-5}$ alkyl, benzyl, $C_{2-5}$ alkoxyalkyl, such as $CH_3OCH_2$, $C_{3-6}$ alkoxyalkoxyalkyl, such as $CH_3OCH_2CH_2OCH_2$, tri-$C_1$-$C_5$-alkylsilyl, such as tert-butyldimethylsilyl or trimethylsilyl, or tetrahydropyranyl with a compound of the formula (III):

wherein $R^1$ is defined above and X is a metal atom or metal complex selected from Li, MgCl, MgBr, $(CuMgCl)_{1/2}$, $(CuMgBr)_{1/2}$, $(CuLi)_{1/2}$, $(CuLi_2CN)_{1/2}$ or $CeCl_2$ to afford a compound of the formula (IV):

(B) hydrolyzing the compound of formula (IV) under acidic conditions to afford a compound of the formula (V):

(C) stereospecifically reducing the ketone function in a compound of formula (V) under standard conditions to afford a compound of the formula (VI):

and (D) lactonizing the compound of the formula (VI) by first saponifying the amide followed by acidic treatment to afford the compound of the formula (I).

In a preferred embodiment, the compounds prepared by the process of this invention are those compounds of the formula (I) wherein $R^1$ is (a) and $R^6$ is hydrogen and R is hydrogen or methyl and b and d represent double bonds or a, b, c and d are single bonds.

In a second preferred embodiment, the compounds prepared by the process of this invention are those compounds of the formula (I) wherein $R_1$ is (b), $R^2$ and $R^3$ independently are chloro, fluoro or methyl and $R^4$ is 4-fluoro-3-methylphenyl or 4-fluorobenzyloxy. The most preferred compounds are those wherein (1) E is —CH=CH—, $R^2$ and $R^3$ are methyl and $R^4$ is 4-fluoro-3-methylphenyl; and (2) E is —CH=CH—, $R^2$ and $R^3$ are methyl and $R^4$ is 4-fluorobenzyloxy.

The reaction of the compound of the formula (II) with the compound of the formula (III) is conducted at a temperature between −78° and −30° C., preferably at −30° C. for a period of from 1 to 2 hours, most preferably 1.5 hours at −30° C., in the presence of an inert solvent. Illustrative of such inert solvents are: ethers or thioethers or mixtures thereof, such as diethyl ether, tetrahydrofuran, dimethoxyethane, dimethylsulfide and the like.

The amounts of reactant that are employed in this reaction may vary between 1.0 and 1.1 equivalents of the compound of the formula (II) to each equivalent of the compound of the formula (III). However, 1.0 equivalents of the compound of the formula (II) are preferred. The compound of the formula (II) wherein $R^5$ is 2-thiopyridinyl and $R^7$ is tert-butyldimethylsilyl; and the compound of the formula (III) wherein X is MgBr are preferred.

The hydrolysis of the compound of the formula (IV) is conducted at elevated temperature between 25° and 80° C., preferably at 70° C., for a period of 8 to 24 hours, preferably 16 hours under aqueous acid conditions. The acids which may be utilized in this reaction include organic acis, such as acetic, propionic, trichloroacetic, toluenesulfonic and the like, and inorganic acids, such hydrochloric sulfuric and the like. The reaction may also be conducted in the presence of water soluble organic solvents, such as tetrahydrofuran, glyme and the like. The preferred aqueous acidic conditions are achieved with acetic acid, water and tetrahydrofuran.

The stereospecific reduction of the compound of the formula (V) is conducted according to the procedures disclosed and claimed in U.S. pat. application Ser. No. 616,530, filed June 4, 1984, now abandoned which employs trialkylborane and sodium borohydride at low temperatures, to afford compounds of the formula (VI).

The lactonization of the compound of the formula (VI) may be conducted by sponifying the amide moiety with an alkali hydroxide in aqueous alcohol and then acidifying the reaction mixture with aqueous acid and azeotropically removing the water from the reaction mixture.

Alternatively, the lactonization of the compound of the formula (VI) is conducted at a temperature between 0° and 25° C., preferably at ambient temperature, for a period of from 1 to 12 hours, preferably 3 hours in an inert solvent with a catalytic amount of an acid. Illustrative of such inert solvents are: hydrocarbons, such as, hexane, toluene, benzene, cyclohexane and the like; and ethers, such as, diethylether, tetrahydrofuran, dimethoxyethane and the like. Illustrative of such acids are organic acids, such as, p-toluenesulfonic, benzenesulfonic and the like and inorganic acids, such as, hydrochloric. The preferred acid utilized in the lactonization is p-toluenesulfonic acid.

The starting materials are either known or readily prepared according to the synthetic pathways described below.

The compounds of the formula (III) wherein $R^1$ is (b) are known in the art (see U.S. Pat. Nos. 4,375,475 and 4,322,563). For the compounds of the formula (III) wherein $R^1$ is (a), Tetrahedron Lett., pp. 1373-6 (1983) and Tetrahedron Lett., pp. 1655-8 (1984) describe procedures for preparing compounds which can be readily converted into the desired compounds using standard chemical transformations.

The compounds of the formula (II), wherein $R^5$ and $R^7$ are defined above, are readily prepared according to the following synthetic pathway from ascorbic acid:

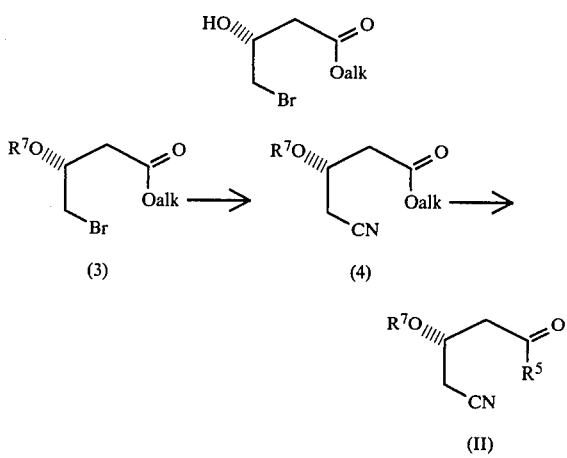

Ascorbic acid (1) is degraded utilizing the methodology of Buck et al., *Acta. Chem. Scand.*, B, 37, 341 (1983) to afford alkyl 4(S)-bromo-3-hydroxy butanoate (2) which is then reacted with an appropriate reagent to protect the hydroxy function and yield the compounds of the formula (3). The compound (3) is reacted with sodium cyanide in an inert solvent to give the compound of the formula (4) which is hydrolyzed and reacted with the appropriate reagent to afford compounds of the formula (II).

The following Examples illustrate the present invention and as such are not to be considered as limiting the invention set forth in the claims appended hereto.

EXAMPLE 1

Preparation of 6-[2-(4'-Fluoro-3,3',5-trimethyl-[1,1'-biphenyl]-2-yl)ethenyl]-3,4,5,6-tetrahydro-4-hydroxy-2H-pyran-2-one

(a): 7-(4'-Fluoro-3,3',5-trimethyl-[1,1'-biphenyl]-2-yl)-3(S)-t-butyldimethylsilyloxy-5-oxo-6(E)-heptenoic acid nitrile (1a)

E-2-(4'-Fluoro-3,3',5-trimethyl-[1,1'-biphenyl]-2-yl)ethenylbromide (1.0 g, 3.1 mmol) was treated with magnesium in (0.1 g, 4.0 mmol) refluxing tetrahydrofuran (15 ml) to form the Grignard reagent. This Grignard reagent was cooled to −78° C. under nitrogen and 4-cyano-3(R)-t-butyldimethylsilyloxybutanoic acid 2-pyridinylthioester (1.0 g, 3.1 mmol) in tetrahydrofuran (5 ml) was added. The reaction mixture was stirred for 30 minutes at −78° C. and warmed to 0° C. over 2 hours. The reaction was quenched with saturated aqueous ammonium chloride (25 ml) and the reaction mixture extracted with methylene chloride (3×25 ml). The organic phases were combined, dried over sodium sulfate and concentrated in vacuo to give the crude product as a yellow oil. The crude product was purified by chromatography over silica gel eluted with acetone:methylene chloride (5:95) to afford the desired product 1(a).

(b): 7-(4'-Fluoro-3,3',5-trimethyl-[1,1'-biphenyl]-2-yl)-3(R)-hydroxy-5-oxo-6(E)-heptenoic acid amide (1b)

The compound 1(a) (1.0 g, 2.3 mmol) was heated at 70° C. for 24 hours in a mixture of acetic acid, tetrahydrofuran and water (4:1:1) and then diluted with water (25 ml). The reaction mixture was extracted with methylene chloride (3×25 ml) and the organic phases combined, dried over sodium sulfate and concentrated in vacuo to afford the desired product 1(b) as a yellow oil.

(c): 7-(4'-Fluoro-3,3',5-trimethyl-[1,1'-biphenyl]-2-yl)-3(R),5(S)-dihydroxy-6(E)-heptenoic acid amide (1c)

A solution of compound 1(b) (1.5 g, 3.9 mmol) and triethylborane (0.46 g, 4.7 mmol) in tetrahydrofuran (11 ml) under nitrogen was cooled to −78°. Sodium borohydride (175 mg, 4.62 mmol) was added followed by the addition of methanol (5 ml) over 15 minutes. The temperature was maintained at −65° during the addition. The reaction was carefully quenched at 20° C. with a solution of 30 percent hydrogen peroxide (15 ml) and water (30 ml). The reaction mixture was extracted with ethyl acetate (50 ml). The organic phase was washed with 1N aqueous hydrochloric acid (25 ml), water (25 ml) and pH 7 buffer solution (25 ml), then dried over sodium sulfate and concentrated in vacuo. The oily residue was crystallized in hexane and triturated in hexane to afford the compound 1(c) as a white solid (m.p. 78°–80° C.). High pessure liquid chromatography assay indicates a purity of 99% of the desired product.

(d): 6-[2-(4'-Fluoro-3,3',5-trimethyl-[1,1'-biphenyl]-2-yl)ethenyl]-3,4,5,6-tetrahydro-4(R)-hydroxy-2H-pyran-2-one To a suspension of the compound 1(c) (10.97 g) in water (60 ml) was added 0.5N sodium hydroxide (142 ml) and the suspension stirred at ambient temperature until a solution was obtained. The solution was diluted with methylene chloride (250 ml) and then acidified with 3N hydrochloric acid (25 ml). The phases were separated and the aqueous phase extracted with methylene chloride (130 ml). The combined organic phase was washed with water (250 ml) and saturated aqueous sodium chloride (250 ml). The aqueous phases were backwashed with methylene chloride (80 ml) and the combined organic phases were dried over sodium sulfate and then concentrated in vacuo at less than 30° C. The residue was dissolved in toluene and heated at 90° C. for 9 hours under nitrogen. The toluene was removed in vacuo and the residue dissolved in diethyl ether (10 ml). To the solution was added hexane (15 ml) and the solution cooled to 0°–5° C. to afford the desired compound as a precipitate. The precipitate was washed with hexane:diethyl ether (3:2) to yield the desired product as a white solid.

EXAMPLE 2

Preparation of 4-Cyano-3(R)-t-butyldimethylsilyloxy butanoic acid, 2-pyridinylthioester

(a): Methyl-4-bromo-3(R)-hydroxybutanoate 2(a)

A solution of ascorbic acid (35.22 g, 0.20 mole) in water (500 ml) was treated with calcium carbonate (40 g, 0.40 mole). The mixture was then stirred at 10° C. and 30 percent hydrogen peroxide (80 ml) was slowly added. The reaction mixture was then allowed to warm slowly to 20° C. at which point the reaction became exothermic. The reaction mixture was then stirred at 45°–50° C. for 40 minutes and then treated with activated carbon (8 g). The reaction was then heated at 95°–100° C. to destroy the excess peroxide. When the solution gave a negative starch-iodide test (about 45 minutes) it was filtered through diatomaceous earth. Treatment of the filtrate with potassium carbonate (13.82 g, 0.10 mol) precipitated the calcium as the carbonate. The calcium carbonate was filtered and the filtrate concentrated in vacuo to about 45 ml. The concentrate was then treated to the slow addition of methanol (400 ml). The potassium-D-threonate that precipitated was collected by filtration.

Compound 2(a) was prepared from potassium-D-threonate in the manner described by Bock et al., Acta. Chem. Scand., 341 (1983).

(b): Methyl 4-bromo-3(R)-t-butyldimethylsilyloxybutanoate (2b)

To the compound (2a) (10 mmol) dissolved in dimethyl formamide (20 ml) at 22°-24° C. was added t-butyldimethylsilylchloride (10.5 mmol) and then imidazole (25 mmol) was added. The reaction was nitrated by the addition of p-dimethylaminopyridine (0.05 mmol) and then stirred for 3 hours at 22° C. The reaction was quenched with water (100 ml) and the reaction mixture extracted with mehylene chloride (2×50 ml). The combined organic phase was washed with water (50 ml) and saturated aqueous sodium chloride (50 ml), dried over sodium sulfate and concentrated in vacuo to yield the compound 2(b) with satisfactory ir and nmr spectra.

(c): Methyl 4-cyano-3(R)-t-butyldimethylsilyloxybutanoate (2c)

To the compound (2a) (3.0 g, 10.0 mmol) dissolved in dimethylsulfoxide (25 ml) was added sodium cyanide (4.9 g, 10.0 mmol). The reaction mixture was stirred for 16 hours at 22°-24° C. and then poured onto water (100 ml). The aqueous solution was extracted with methylene chloride (2×50 ml). The combined organic extracts were washed with water (50 ml) and saturated aqueous sodium chloride (50 ml), dried over sodium sulfate and concentrated in vacuo to yield compound 2(c) with satisfactory ir and nmr spectra.

(d): 4-Cyano-3(R)-t-butyldimethylsilyloxybutanoic acid (2d)

To the compound 2(c) dissolved in 50 percent aqueous methanol (5 ml) was added 1N sodium hydroxide (1 ml). The reaction mixture was stirred for 3 hours at 22°-24° C. and then the methanol was removed in vacuo. The residue was diluted with water (15 ml) and acidified with oxalic acid to a pH 3.0. The aqueous solution was extracted with methylene chloride (2×20 ml), the combined extracts dried over sodium sulfate and concentrated in vacuo to give compound 2(d) as an oil with satisfactory ir and nmr spectra.

(e): 4-Cyano-3(R) -t-butyldimethylsilyloxybutanoic acid, 2-pyridinylthioester

To the compound 2(d) (277 mg, 1.0 mmol) dissolved in acetonitrile (5 ml) was added 2,2'-dipyridyldisulfide (244 mg, 1.1 mmol) and triphenylphosphine (288 mg, 1.1 mmol). The reaction mixture was stirred for 2 hours at 22°-24° C. and then the acetonitrile removed in vacuo. The residue was purified by column chromatography over silica gel eluted with methylene chloride:-hexane (1:3) to give the desired product as an oil with satisfactory ir and nmr spectra.

EXAMPLES 3-12

Utilizing the general procedures of Example 1 and starting from the appropriately substituted compounds of the formula (III) and 4-cyano-3(R)-t-butyldimethyl-silyloxybutanoic acid, 2-pyridinylthioester the following compounds of the formula (I) are prepared:

| Compound Number | $R^1$ |
|---|---|
| 10 | 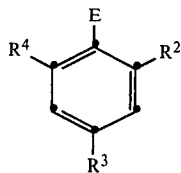 |
| 11 | 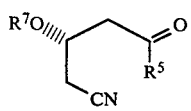 |
| 12 |  |

What is claimed is:

1. A process for the preparation of compounds of the following structural formula (I):

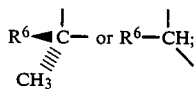 (I)

wherein $R^1$ is selected from the group consisting of:

(a)

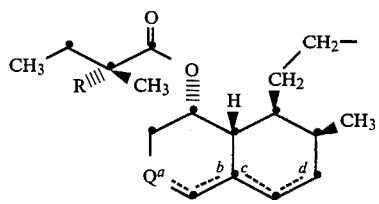

wherein
Q is

R⁶◀C— or R⁶—CH;
   ‖
   CH₃

$R^6$ is H or OH;

R is hydrogen or methyl, and a and c except when $R^6$ is OH or b and d represent double bonds or all of a, b, c and d are single bonds; or (b)

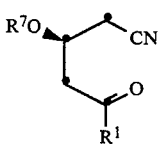

wherein E is —$CH_2$—, —$CH_2CH_2$— or —CH=CH—; $R^2$ and $R^3$ independently are $C_{1-3}$ alkyl fluoro, chloro or bromo; and $R^4$ is phenyl, benzyloxy, substituted phenyl or substituted benzyloxy in which the phenyl group in each case is substituted with one or more substituents selected from $C_{1-3}$ alkyl, fluoro, bromo or chloro;

which comprises:

(A) reacting a compound of the formula (II):

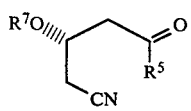 (II)

wherein $R^5$ is $C_{1-5}$ alkyloxy, benzyloxy or 2-thiopyridinyl; and $R^7$ is $C_{1-5}$ alkyl, benzyl, $C_{2-5}$ alkoxyalkyl, $C_{3-6}$ alkoxyalkoxyalkyl, tri-$C_1$-$C_5$-alkylsilyl or tetrahydropyranyl with a compound of the formula (III):

$R^1X$ (III)

wherein $R^1$ is defined above; and X is a metal atom or metal complex selected from Li, MgCl, MgBr, $(CuMgCl)_{1/2}$, $(CuMgBr)_{1/2}$, $(CuLi)_{1/2}$, $(CuLi_2CN)_{1/2}$ or $CeCl_2$ to afford a compound of the formula (IV):

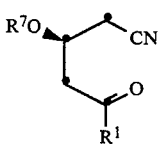 (IV)

(B) hydrolyzing the compound of the formula (IV) under acidic conditions to afford a compound of the formula (V):

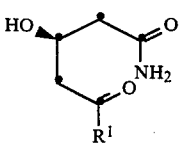 (V)

(C) stereospecifically reducing the ketone function in a compound of the formula (V) with tri-$C_{1-5}$-alkylborane and alkali metal borohydride at low temperatures to afford a compound of the formula (VI):

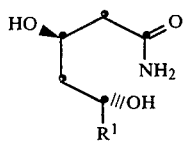

(D) lactonizing the compound of the formula (VI) by first saponifying the amide followed by acidic treatment to afford the compound of the formula (I).

2. A process of claim 1 wherein $R^1$ is (a).

3. A process of claim 2 wherein $R_6$ is hydrogen and R is hydrogen or methyl and b and d represent double bonds or each of a, b, c and d is a single bond.

4. A process of claim 1 wherein $R^1$ is (b).

5. A process of claim 4 wherein $R^2$ and $R^3$ independently are chloro, fluoro or methyl and $R^4$ is 4-fluoro-3-methylphenyl or 4-fluorobenzyloxy.

6. A process of claim 5 wherein E is —CH=CH—, $R^2$ and $R^3$ are methyl.

7. A process of claim 5 wherein E is —CH=CH—; $R^2$ and $R^3$ are methyl and $R^4$ is 4-fluoro-3-methylphenyl.

8. A process for the preparation of a compound of the formula (V) which comprises the Steps (A) and (B) of claim 1.

9. A process for the preparation of an compound of the formula (VI) which comprises the Steps (A), (B) and (C) of claim 1.

* * * * *